(12) United States Patent
Chesbrough et al.

(10) Patent No.: US 7,424,320 B2
(45) Date of Patent: Sep. 9, 2008

(54) TISSUE LOCALIZING AND MARKING DEVICE AND METHOD OF USING SAME

(75) Inventors: Richard M. Chesbrough, Bloomfield Hills, MI (US); Steven E. Field, Grand Rapids, MI (US); Ryan L. Goosen, Coopersville, MI (US)

(73) Assignees: Bard Peripheral Vascular, Inc., Tempe, AZ (US); Bard Shannon Limited, Nieuwegein (NL)

( * ) Notice: Subject to any disclaimer, the term of this patent is extended or adjusted under 35 U.S.C. 154(b) by 629 days.

(21) Appl. No.: 10/707,044

(22) Filed: Nov. 17, 2003

(65) Prior Publication Data

US 2004/0116805 A1 Jun. 17, 2004

Related U.S. Application Data

(60) Provisional application No. 60/427,048, filed on Nov. 18, 2002.

(51) Int. Cl.
*A61B 6/00* (2006.01)
(52) U.S. Cl. .................. 600/431; 600/414; 600/420; 600/426; 606/167; 606/185; 606/151; 606/230; 604/93.01
(58) Field of Classification Search ................. 600/431, 600/562; 606/185
See application file for complete search history.

(56) References Cited

U.S. PATENT DOCUMENTS 5,059,197 A 10/1991 Urie et al.
6,228,055 B1 * 5/2001 Foerster et al. ............. 604/116
6,234,177 B1 5/2001 Barsch
7,044,957 B2 * 5/2006 Foerster et al. ............. 606/185
2001/0034528 A1 * 10/2001 Foerster et al. ............. 606/116
2002/0026201 A1 * 2/2002 Foerster et al. ............. 606/116
2002/0193815 A1 * 12/2002 Foerster et al. ............. 606/151
2004/0024304 A1 * 2/2004 Foerster et al. ............. 600/407
2005/0049489 A1 * 3/2005 Foerster et al. ............. 600/431
2005/0165305 A1 * 7/2005 Foerster et al. ............. 600/431
2006/0074443 A1 * 4/2006 Foerster et al. ............. 606/185

FOREIGN PATENT DOCUMENTS

| EP | 0769281 A2 | 4/1997 |
| EP | 1163888 A1 | 12/2001 |
| EP | 1304085 A2 * | 4/2003 |
| WO | WO 9608208 A1 * | 3/1996 |
| WO | 0100101 A1 | 1/2001 |
| WO | 0108578 A1 | 2/2001 |

* cited by examiner

*Primary Examiner*—Brian L. Casler
*Assistant Examiner*—Parikha S Mehta (57) ABSTRACT

A delivery apparatus for the percutaneous placement of a medical device at an area of interest in a tissue mass comprises an introducer comprising a cannula having an insertion tip, an expulsion opening near the insertion tip, and a medical device within the cannula comprising an imaging element, and a guide element connected to the imaging element and having a separable portion, and wherein the cannula is inserted into the tissue mass such that the medical device can be expelled through the expulsion opening into the tissue mass, and when the cannula is withdrawn from the tissue mass, the imaging element is placed within the tissue mass at the area of interest, and at least part of the guide element extends exteriorly of the tissue mass, and when the separable portion is separated from the guide element, no part of the guide element extends exteriorly of the tissue mass.

69 Claims, 11 Drawing Sheets

TISSUE LOCALIZING AND MARKING DEVICE AND METHOD OF USING SAME

CROSS REFERENCE TO RELATED APPLICATIONS

This application claims the benefit of U.S. provisional application Ser. No. 60/427,048, filed Nov. 18, 2002, which is incorporated herein in its entirety.

BACKGROUND OF THE INVENTION

1. Field of the Invention

The invention relates generally to a combined percutaneous imaging marker and localizing wire for imaging and surgically identifying an area of interest within a tissue mass. More particularly, the invention relates to a combined percutaneous imaging marker and localizing wire having a connection enabling separation of the localizing wire from the imaging marker after placement of the imaging marker in the tissue mass.

2. Description of the Related Art

Tissue biopsy using a biopsy cannula is a well-known procedure for diagnosing the presence of a malignancy in a tissue mass comprising a tissue anomaly, such as a lesion. If the results of the biopsy indicate the presence of a malignancy, a follow-up surgical procedure involving excision of the lesion is frequently performed. In certain tissue masses, such as breast tissue, it may be difficult to locate the lesion through palpation or visual observation. Contemporary imaging techniques can image a lesion slightly larger than the size of a subsequent biopsy specimen. Thus, after the biopsy specimen is taken, the remaining lesion can be too small to be imaged, making it difficult to find the lesion for surgical excision.

This is particularly true of suspected breast tissue malignancies, where the accepted medical approach is to evaluate and, if necessary, treat the suspected malignancy at the earliest possible time. To ensure that the lesion can be located after the biopsy, a marker is frequently inserted into the tissue mass through the biopsy cannula to locate the lesion for further evaluation using imaging techniques, such as radiography, ultrasound, or MRI. The sole purpose of the marker is to provide an imageable reference for locating the lesion.

If subsequent evaluation of the biopsy sample reveals the absence of a malignancy, the marker is typically used for follow-up evaluation at a subsequent time, which may be several months, to confirm either the continued absence of a malignancy or the development of a further change in the tissue mass indicating the need for further evaluation.

If subsequent evaluation of the biopsy sample reveals the presence of a malignancy, surgery is frequently performed. While the marker can locate the lesion through imaging techniques, it is inadequate as a guide for the surgeon to quickly locate the lesion with minimal trauma to the surrounding tissue. Consequently, a localizing wire is typically inserted with the marker being used to guide the insertion of the localizing wire. The localizing wire has a metal shaft that terminates in a folded portion forming an anchor for anchoring the localizing wire in the tissue mass. The shaft extends from the anchoring structure to the exterior of the body to be followed by the surgeon in locating the lesion. The localizing wire is typically removed during the surgery.

The decision to perform surgery is typically made after the biopsy has been taken and the marker has been placed. Thus, it is necessary to place the localizing wire in a separate procedure, again involving the insertion of a cannula into the tissue mass. This can be an extremely painful procedure for the patient. The procedure is also time-consuming and costly. Additionally, while the marker is used to relocate the lesion for placement of the localizing wire, it is still possible to mislocate the localizing wire, particularly if the marker has moved. In such a case, the lesion may not be sufficiently excised, or excess, healthy tissue may be unnecessarily excised.

It would be convenient for the patient if the separate insertion procedure for the localizing wire could be eliminated upon a determination that the biopsy specimen was malignant. It would be an improvement, both in cost and patient health, if the surgical excision of the lesion could be accomplished without the intervening insertion of the localizing wire.

SUMMARY OF THE INVENTION

A medical device comprises an imaging element for subcutaneous placement in a tissue mass to identify an area of interest in the tissue mass, and a guide element connected to the imaging element and having a separable portion, wherein, when the imaging element is placed within the tissue mass, at least part of the guide element extends exteriorly of the tissue mass to permit the locating of the area of interest, and when the separable portion is separated from the guide element, no part of the guide element extends exteriorly of the tissue mass. The separable portion can comprise any portion of the guide element, including the entire guide element.

The imaging element can be imaged by any imaging techniques, an illustrative listing of which includes: x-ray, ultrasound, magnetic resonance imaging (MRI), computer assisted tomography (CAT), mammography, fluoroscopy, Doppler, other roentgenological imaging methods, visualization, and detection of emission. The imaging element and guide element can comprise a portion that is one of bioabsorbable or non-bioabsorbable. The imaging and guide elements can be entirely bioabsorbable or non-bioabsorbable.

Preferably, the imaging element comprises a first portion that is non-bioabsorbable and a second portion that is bioabsorbable. The first portion can be made of a suitable metal, such as titanium, and the second portion can be made of a material such as collagen.

The imaging element can further comprise at least one extension, with a bioabsorbable element mounted to the extension. The bioabsorbable element can encapsulate at least a portion of the extension.

The imaging element can define a guide element opening through which the guide element passes. Preferably, a loop formed in the imaging element defines the guide element opening. The guide element is preferably a filament, which can be made from a bioabsorbable material or a suture material. The filament can alternatively be a metal wire.

A holder can be mounted to a portion of the guide element exterior of the tissue mass to hold the position of the guide element relative to the tissue mass.

A releasable connection can connect the guide element to the imaging element to define the separable portion. The releasable connection can comprise a threaded coupling, a weldment, a severable portion of the guide element, or a discontinuity in the guide element.

A gripping element can be attached to the guide element for separating the guide element from the imaging element.

Another embodiment relates to a method for localizing and marking an area of interest in a tissue mass, the method comprising the steps of providing a medical device comprising an imaging element and a guide element connected to the imaging element, inserting the medical device into the tissue mass so that at least part of the guide element extends exteriorly of the tissue mass, and removing at least a portion of the guide element so that no portion of the guide element extends exteriorly of the tissue mass.

In yet another embodiment, the invention relates to a delivery apparatus for the percutaneous placement of a medical device at an area of interest in a tissue mass to facilitate subsequent determination of the area of interest, the delivery apparatus comprising an introducer comprising a cannula defining a lumen and having a proximal end, a distal end forming an insertion tip, and an expulsion opening near the insertion tip, a stylet having a distal end slidably received within the lumen, and when the delivery apparatus is in a ready position, the distal end is spaced inwardly from the insertion tip to form a recess between the distal end and the insertion tip, and a medical device positioned within the recess comprising an imaging element for subcutaneous placement in a tissue mass to identify an area of interest in the tissue mass, and a guide element connected to the imaging element and having a separable portion, wherein the cannula is inserted into the tissue mass such that when the stylet is advanced into the recess, the medical device is expelled through the expulsion opening into the tissue mass, and when the cannula is withdrawn from the tissue mass, the imaging element is placed within the tissue mass at the area of interest, and at least part of the guide element extends exteriorly of the tissue mass, and when the separable portion is separated from the guide element, no part of the guide element extends exteriorly of the tissue mass.

DESCRIPTION OF EMBODIMENTS OF THE INVENTION

Figure 1:
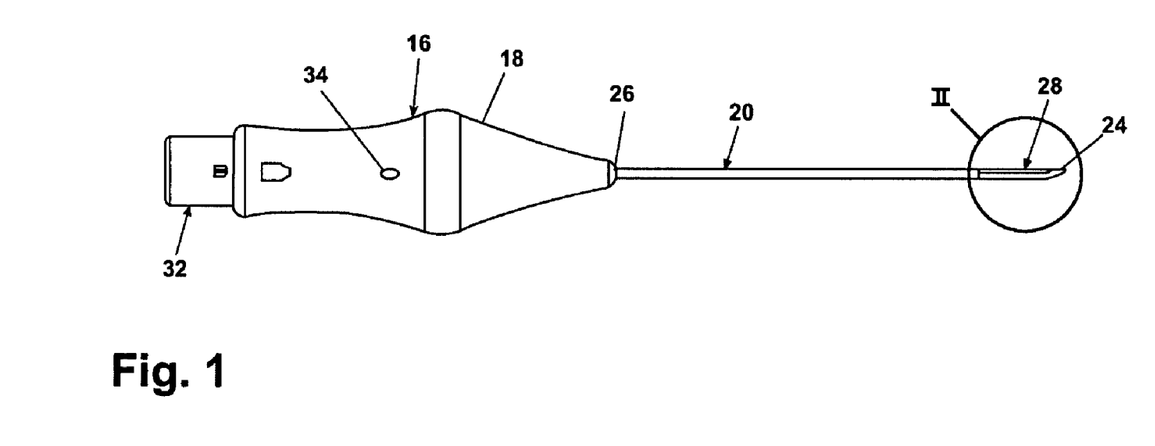
FIG. 1 is an elevational view of an introducer for inserting a medical device in the form of a combination localizing and marking apparatus according to the invention.
Figure 2:
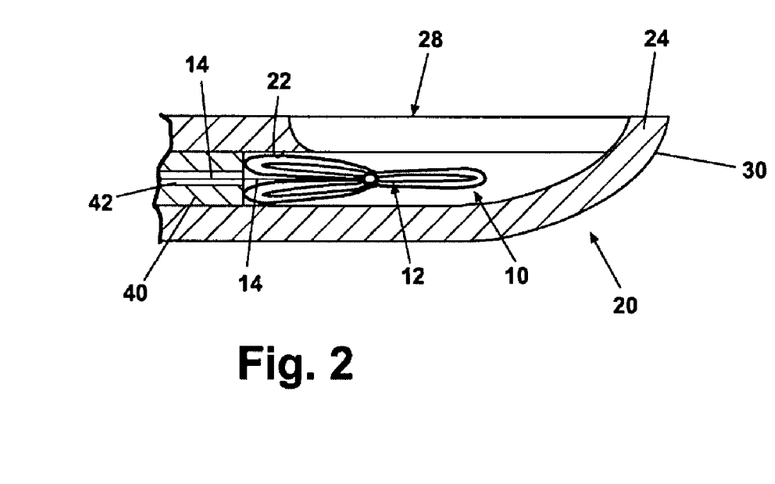
FIG. 2 is an enlarged sectional view of a portion of the introducer of FIG. 1 showing the combination localizing and marking apparatus therein contained within a recess in the introducer.
Figure 3:
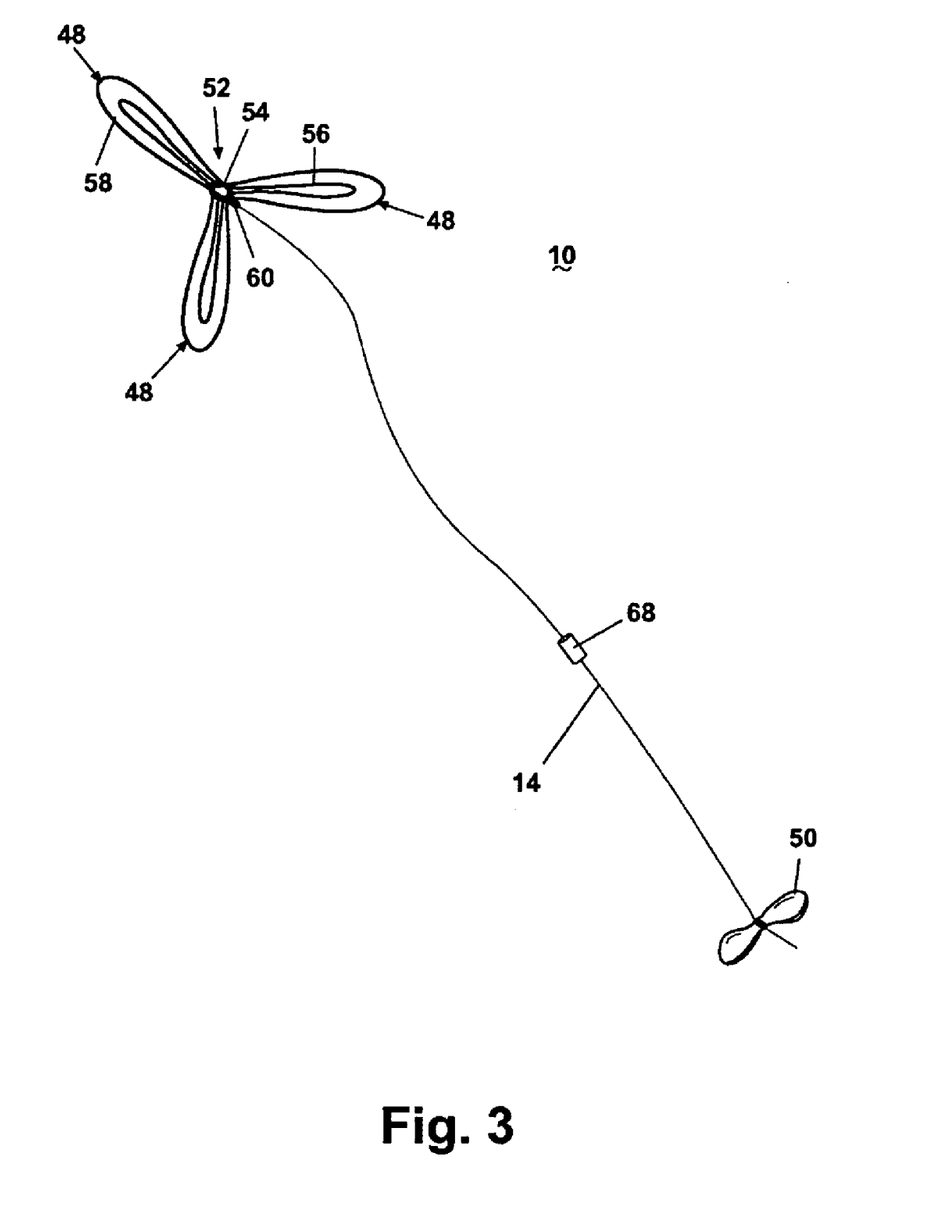
FIG. 3 is a perspective view of the combination localizing and marking apparatus shown in FIG. 2 comprising an embodiment of an imaging element and a guide element, with the guide element being removable from the imaging element through a releasable connection.

Referring now to the drawings, and specifically to FIGS. 1-3, an introducer 16 housing a medical device 10 according to the invention. The medical device 10 is shown comprising an imaging element 12 and a guide element 14. The medical device 10 is placed in a tissue mass with the introducer 16, which may comprise any well-known introducing device sufficient for the purposes described herein.

For illustration purposes, the introducer 16 is shown comprising a handle 18 and a cannula 20. As shown in FIG. 1, the cannula 20 has a distal end 24, and a proximal end 26 attached to the handle 18. The cannula 20 comprises a lumen 22 through which the medical device 10 is conveyed for placement in the tissue mass. The introducer 16 also comprises a generally well-known plunger 32 that is slidable relative to the handle 18.

The cannula 20 is shown in FIGS. 1 and 2 terminating at the distal end 24 in a closed insertion tip 30 which is adapted in a well-known manner for ease of insertion of the cannula 20 into the tissue mass. Adjacent the insertion tip 30 is an expulsion opening 28 in the wall of the cannula 20 in fluid communication with the lumen 22 adapted for expulsion of the medical device 10 from the lumen 22. A piston 40, referred to herein as a stylet, is in slidable register with the lumen 22. A proximal end of the stylet 40 is mounted to the plunger 32, such that the slidable movement of the plunger 32 effects a similar movement of the stylet 40. A distal end of the stylet 40 is spaced from the insertion tip 30 to define a recess within the cannula 20 that receives the medical device 10 as best seen in FIG. 2. The sliding of the plunger 32 relative to the handle 18 slides the plunger 32 into the recess and forces the medical device 10 out the expulsion opening 28.

While the cannula 20 is shown with a side or lateral expulsion opening 28, the cannula 20 could just as easily have an end or axial opening formed by extending the lumen through the insertion tip 30. With this configuration, the medical device 10 is axially expelled instead of laterally expelled from the cannula 20.

As shown in FIG. 2, a guide element bore 42 extends coaxially through the stylet 40 for receipt of the guide element 14 as hereinafter described. The handle 18 is provided with a guide element aperture 34 in fluid communication with the guide element bore 42 for receipt of the guide element 14. Alternatively, the stylet 40 can be provided with a radial slot (not shown) extending longitudinally the length of the stylet 40 and fluidly communicating with the guide element aperture 34 for receipt of the guide element 14, rather than the guide element bore 42.

Referring now specifically to FIG. 3, a first embodiment 52 of the imaging element is shown for illustrative purposes as comprising three radially-aligned, elongated extensions 48, each comprising a non-bioabsorbable portion 56 and a bioabsorbable portion 58 regularly spaced about a center hub 54. The elongated extensions 48 preferably perform dual functions of being imageable and anchoring the imaging element 52 in the tissue mass. The bioabsorbable portion 58 is used to enhance the imageability of the imaging element 52 in an imaging method different from the extensions 48.

For example, the non-bioabsorbable portion 56 can comprise a metal, such as titanium, tungsten or a ferromagnetic material, and is preferably most easily imageable using x-ray, while the bioabsorbable portion 58 can be collagen or gelatin, which is most easily imageable using ultrasound. While these materials are preferred, the imaging element 52 can be made from any suitable imaging material and imaged using any one of the following common imaging techniques: x-ray, ultrasound, magnetic resonance imaging (MRI), computer assisted tomography (CAT), mammography, fluoroscopy, Doppler, other roentgenological imaging methods, visualization, and detection of emission. Unless otherwise indicated, further references to one or more specific imaging techniques is intended for illustrative purposes and not as a limitation.

Although FIG. 3 illustrates an imaging element 52 comprising a non-bioabsorbable portion 56 and a bioabsorbable portion 58, the imaging element 52 can be fabricated entirely of a non-bioabsorbable material, or entirely of a bioabsorbable material. If the imaging element 52 is fabricated entirely of a non-bioabsorbable material, imaging may be restricted to a specific techniques such as radiography. Alternatively, if the imaging element 52 is fabricated entirely of a bioabsorbable material, imaging may be restricted to ultrasound. The selection of a non-bioabsorbable material and/or a bioabsorbable material for the imaging element 52 is expected to take into account the future disposition of the imaging element 52 in the tissue mass, as well as the preferred imaging technique. The bioabsorbable portion 56 is illustrated in the Figures as comprising a translucent material, which is the preferred embodiment. However, the bioabsorbable portion 56 can alternatively comprise an opaque material.

The guide element 14 is shown comprising a thin, filament body, such as a thin, titanium wire, a suture, or the like. It is anticipated that the guide element 14 will comprise a structure that functions to guide a surgeon to the biopsy site, in the same manner as a traditional localizing wire. If a suture material is used, it can comprise a bioabsorbable suture. The guide element 14 is attached to the imaging element 52 through a releasable connection 60 which is adapted for selective separation of the guide element 14 from the imaging element 52.

Figure 4A:
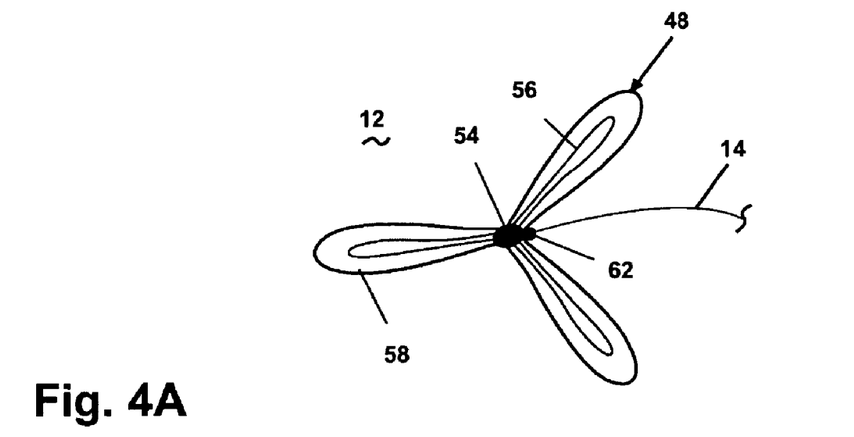
FIG. 4A is an enlarged view of the imaging element shown in FIG. 3 illustrating a first embodiment of the releasable connection.
Figure 4B:
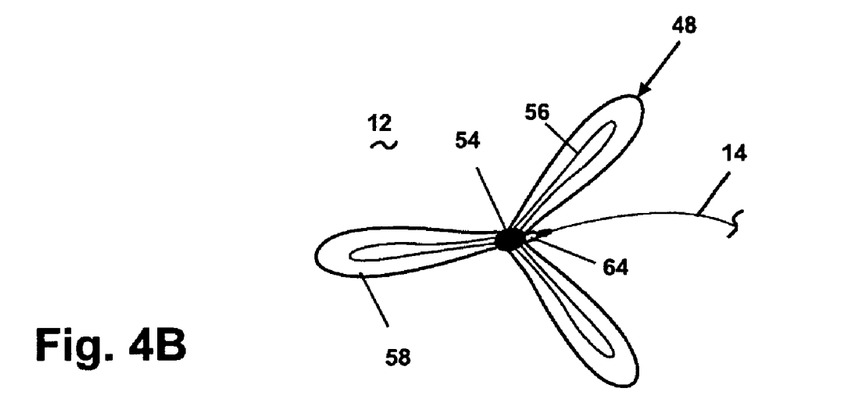
FIG. 4B is an enlarged view of the imaging element shown in FIG. 3 illustrating a second embodiment of the releasable connection.

The releasable connection 60 can take one of several different structures. For example, as illustrated in FIG. 4A, the releasable connection 60 can comprise a spot weld 62 on the guide element 14 at or near the hub 54. The spot weld 62 results in a localized weakness in the guide element 14 enabling the guide element 14 to be separated at that point. As illustrated in FIG. 4B and FIG. 4D, the releasable connection 60 can also comprise a threaded connection 64, in which the end of the guide element 14 is provided with male threads and the hub 54 is provided with cooperating female threads. The guide element 14 is threaded to the imaging element 52 for insertion into the tissue mass. Twisting of the guide element 14 after insertion will unthread the guide element 14 from the imaging element 52 for removal of the guide element 14 from the tissue mass.

Figure 4C:
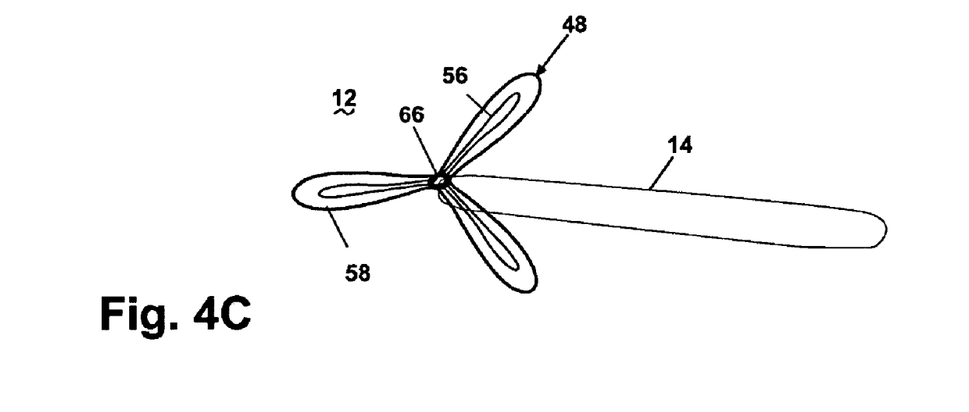
FIG. 4C is an enlarged view of the imaging element shown in FIG. 3 illustrating a third embodiment of the releasable connection and an alternate embodiment of the guide element comprising a filament loop.
Figure 4D:
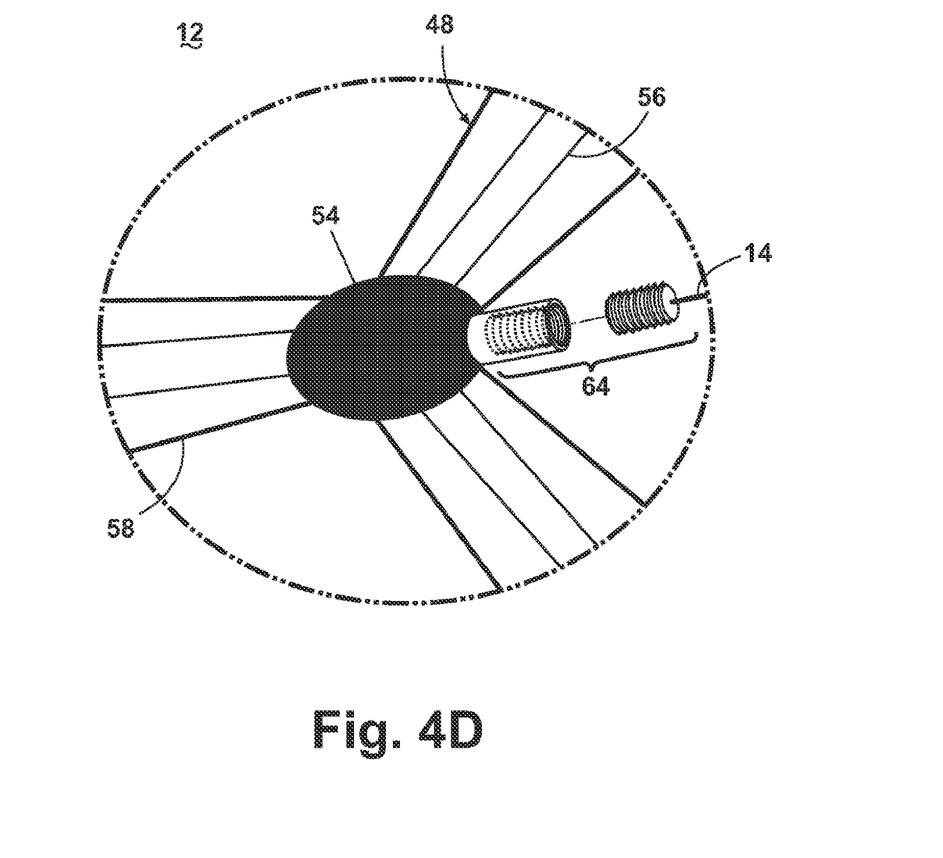
FIG. 4D is an enlarged view of the releasable connection shown in FIG. 4B shown in a released state.

As illustrated in FIG. 4C, the hub 54 can comprise a ring 66, or alternatively can be provided with a loop portion extending therefrom, through which the guide element 14 can be threaded, similar to the threading of a needle. The guide element 14 can comprise a filament loop passing through the ring 66 and extending exteriorly of the tissue mass. The guide element 14 can be separated from the imaging element 12 by cutting the filament loop to form two strands and then pulling on one of the strands.

Other suitable separation configurations can be employed, such as a notch, an indentation, or a narrowing of the guide element 14 at the desired point of separation, providing a localized weakness or discontinuity in the guide element 14. Twisting of the guide element 14 will separate the guide element 14 at the localized weakness, similar to the spot weld. Alternatively, the guide element 14 can be separated by first depressing the tissue mass surrounding the guide element 14 in order to reveal a sufficient length of the guide element 14 otherwise engulfed within the tissue mass. The guide element 14 can then be separated at a point adjacent the depressed tissue mass by severing the guide element 14. When the tissue mass rebounds, no portion of the guide element 14 will extend beyond the tissue mass. With such a configuration, it is preferred that the guide element be bioabsorbable. It will be understood that the separation techniques described herein are intended to be illustrative only, and that other separation techniques are feasible and are within the scope of the herein-described inventive concept.

FIGS. 5A-E illustrate several different embodiments of the imaging element 12.

Figure 5A:
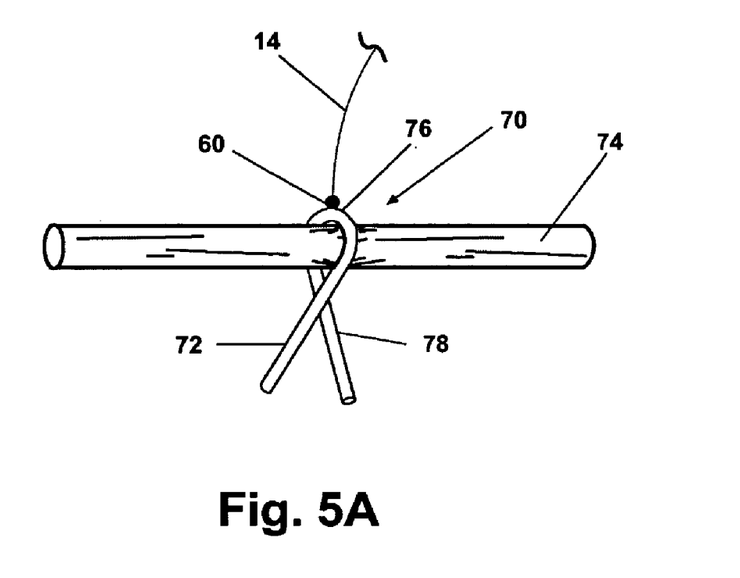
FIG. 5A is an enlarged view of a second embodiment of the imaging element shown comprising a non-bioabsorbable portion and a bioabsorbable portion.

FIG. 5A illustrates an imaging element 70 having the general shape of the Greek letter alpha, and comprising a loop 76 of non-bioabsorbable, wire-like material 72 terminating in a pair of legs 78. The guide element 14 is connected to the imaging element 70 through one of the aforementioned releasable connections 60. The releasable connection 60 can be located at the loop 76, one of the legs 78, or other suitable location on the non-bioabsorbable portion 72. Another non-bioabsorbable portion 74 comprises a flexible, elongated, cylindrical rod adapted for insertion through the loop 76. The second non-bioabsorbable portion 74 can be folded and/or compressed for insertion into the cannula 20, to be expanded when the medical device 10 is ejected into the tissue mass. The non-bioabsorbable portion 74 is preferably a foam material having air pockets that are very imageable using ultrasound techniques, as previously discussed, whereas the metal alpha-shaped portion is very imageable using x-ray. Alternatively, the rod-shaped portion 74 can comprise a bioabsorbable material that can be imaged using ultrasound techniques.

Figure 5B:
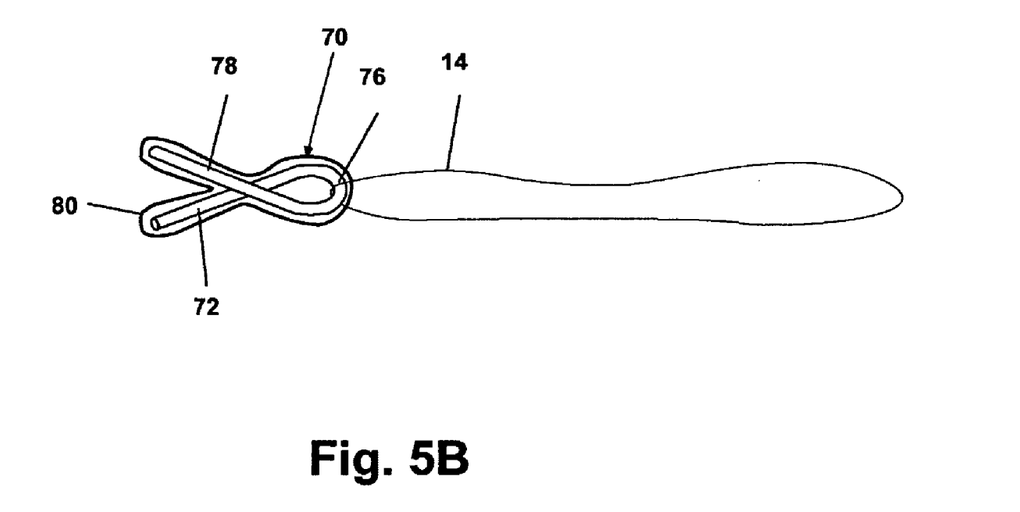
FIG. 5B is an enlarged view of a third embodiment of the imaging element comprising a non-bioabsorbable portion and a bioabsorbable portion, and an alternate embodiment of the guide element.

FIG. 5B illustrates an alpha-shaped imaging element 70 comprising a loop 76 of the non-bioabsorbable, wire-like material 72 terminating in a pair of legs 78. Again, the guide element 14 is connected to the imaging element 70 through one of the aforementioned releasable connections 60. A bioabsorbable portion 80 comprises a bioabsorbable material, such as collagen or gelatin, applied in a generally uniform coating over the entire non-bioabsorbable portion 72. Alternatively, the bioabsorbable portion 80 can comprise a coating extending only over a portion of the imaging element 70, such as the legs 78. FIG. 5B illustrates a releasable connection 60 comprising a filament loop extending through the loop 76 in a manner similar to the configuration illustrated in FIG. 4C.

Figure 5C:
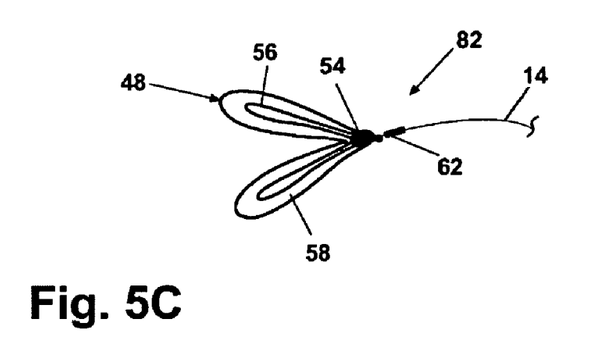
FIG. 5C is an enlarged view of a fourth embodiment of the imaging element comprising a non-bioabsorbable portion and a bioabsorbable portion.
Figures 5D, 5E:
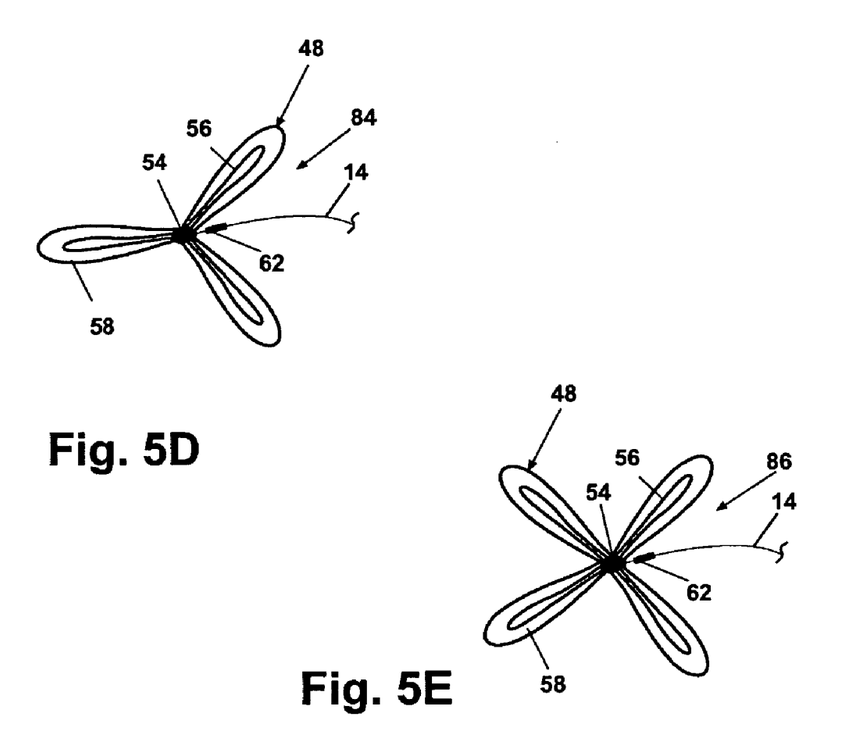
FIG. 5D is an enlarged view of the embodiment of the imaging element shown in FIG. 3 comprising a non-bioabsorbable portion and a bioabsorbable portion.
FIG. 5E is an enlarged view of a fifth embodiment of the imaging element comprising a non-bioabsorbable portion and a bioabsorbable portion.

FIGS. 5C-E illustrate variations of the imaging element 12 illustrated in FIG. 3, comprising a dual extension imaging element 82 (FIG. 5C), a treble extension imaging element 84 (FIG. 5D), and a four bladed imaging element 86 (Figure E). The guide element 14 can be connected to the imaging elements 82-86 through any of the releasable connections previously described herein.

Figure 6A:
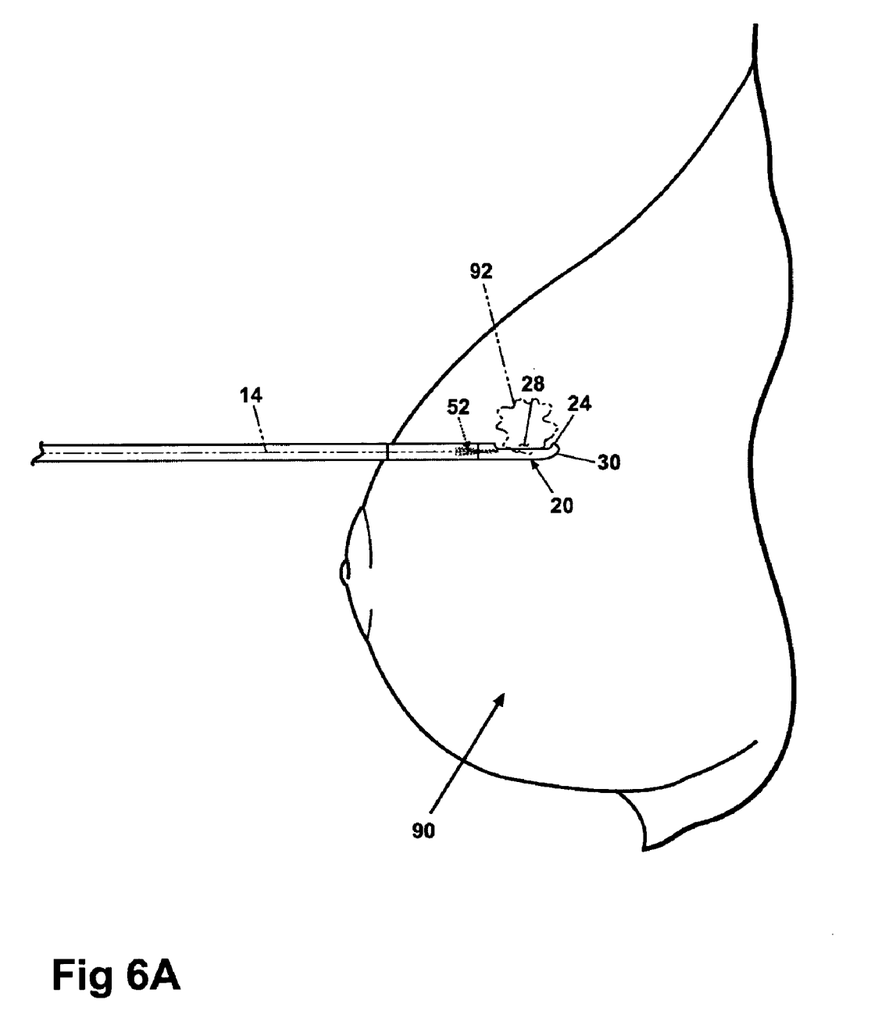
FIG. 6A is a perspective view illustrating the insertion of the introducer into breast tissue to mark and localize a tissue anomaly in the form of a lesion with the combination localizing and marking apparatus.
Figure 6B:
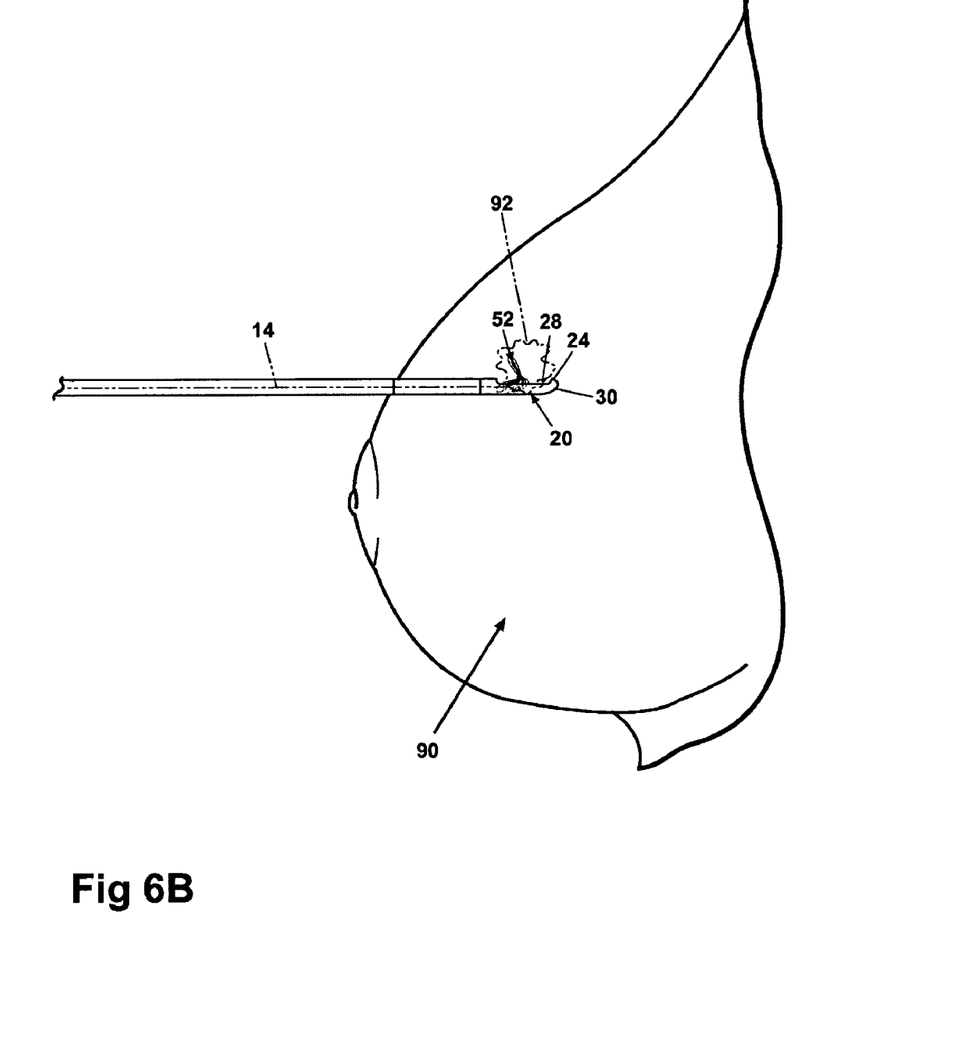
FIG. 6B is a perspective view illustrating the initiation of the expulsion of the combination localizing and marking apparatus at the lesion once the introducer is properly located relative to the lesion.
Figure 6C:
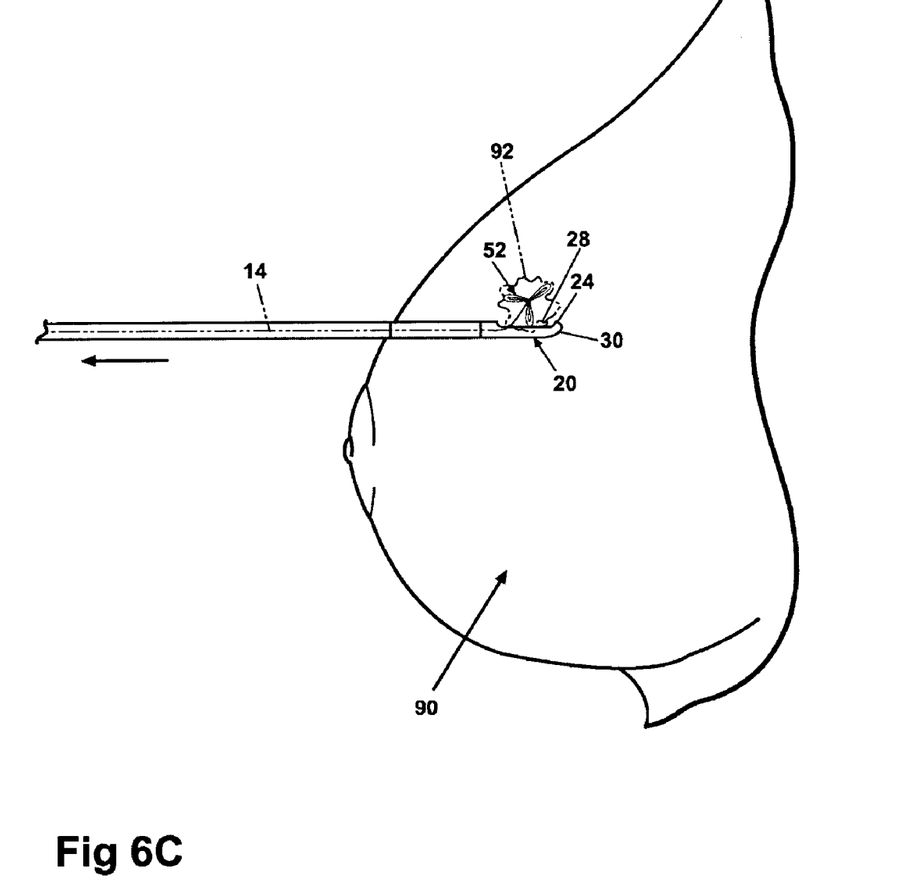
FIG. 6C is a perspective view illustrating the complete expulsion of the the combination localizing and marking apparatus at its placement at the lesion in the breast tissue mass.

FIGS. 6A-C illustrate the placement of the medical device 10 at a biopsy site 92 in a tissue mass 90. Initially, as illustrated in FIGS. 1 and 2, the medical device 10 is inserted into the cannula 20 in preparation for ejection through the expulsion opening 28 with movement of the stylet 40 through the action of the plunger 32. Preferably, the introducer 16 is manufactured with the imaging element 12 loaded in the recess, such that the medical technician does not have to load the imaging element 12.

As illustrated, when loaded, the guide element 14 extends through the guide element bore 42 and out the guide element aperture 34. However, the guide element 14 could also have the end opposite the imaging element 12 freely contained within the guide element bore 42 or releasably attached to the stylet 40.

As illustrated in FIG. 6A, the cannula 20 is inserted into the tissue mass 90 until the insertion tip 30 and the expulsion opening 28 are adjacent the biopsy site 92. It is anticipated that this procedure will immediately follow the recovery of a biopsy sample from the biopsy site 92, and that the cannula 20 will be inserted through a biopsy cannula (not shown) previously emplaced during the biopsy procedure. However, the cannula 20 can be inserted directly into the tissue mass 90 without the use of a biopsy cannula.

Once the cannula 20 is properly positioned, the imaging element 52 is then ejected through the expulsion opening 28 by sliding the plunger 32 which urges the stylet 40 toward the expulsion opening 28, thereby ejecting the imaging element 52 at the biopsy site 92, as illustrated in FIG. 6B.

The cannula 20, and the biopsy cannula if present, is then removed from the tissue mass 90, as illustrated in FIG. 6C, leaving the imaging element 52 in place and the guide element 14 extending through the cannula insertion line to the exterior of the tissue mass 90. The guide element 14 can be further secured in place by a holder 68, also referred to as a clip, which is positioned around the guide element 14 exterior of and in contact with the tissue mass, as shown in FIG. 7.

Figure 7:
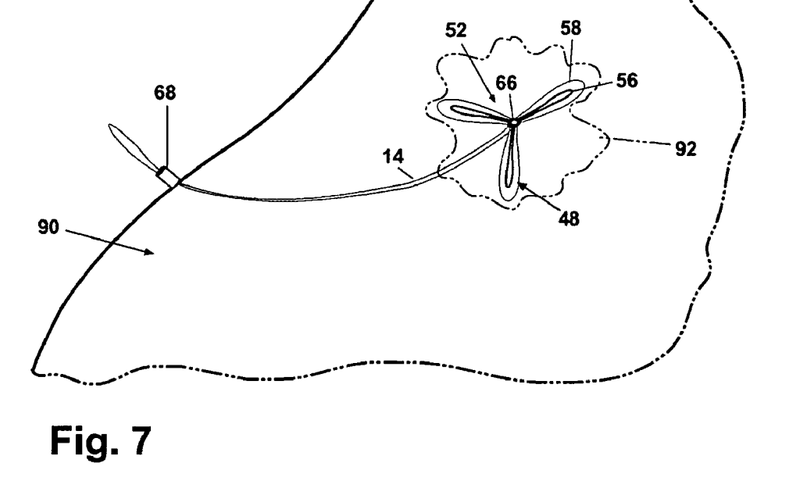
FIG. 7 is an enlarged view of the combination localizing and marking apparatus after placement in the tissue mass and withdrawal of the introducer and showing the imaging element at the lesion and the guide element extending exteriorly of the body.
Figure 8:
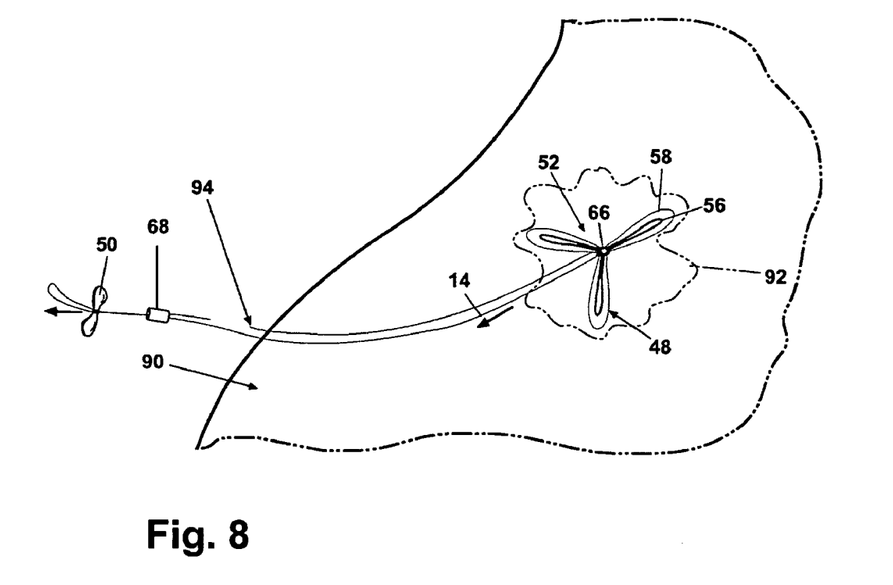
FIG. 8 is an enlarged view of the combination localizing and marking apparatus of FIG. 3 showing the imaging element at the lesion and the guide element being removed from the tissue mass after separation from the imaging element at the releasable connection.

The emplaced medical device 10 is illustrated in FIG. 7. If further diagnosis indicates that surgical intervention is unnecessary, the guide element 14 can be separated from the imaging element 52 by attaching a guide element grip 50 to the guide element 14 to aid in removing the guide element 14. As an illustration, the guide element 14 is shown in FIG. 8 as a loop, one strand of which is severed at a separation point 94. The guide element grip 50 can be attached to the external end of the loop to facilitate the pulling of the guide element 14 from the ring 66. The imaging element 52 will remain in place for future imaging, if necessary. The bioabsorbable portion 58 will be slowly adsorbed into the surrounding tissue mass 90, leaving the non-bioabsorbable portion 56 in place.

Figure 9:
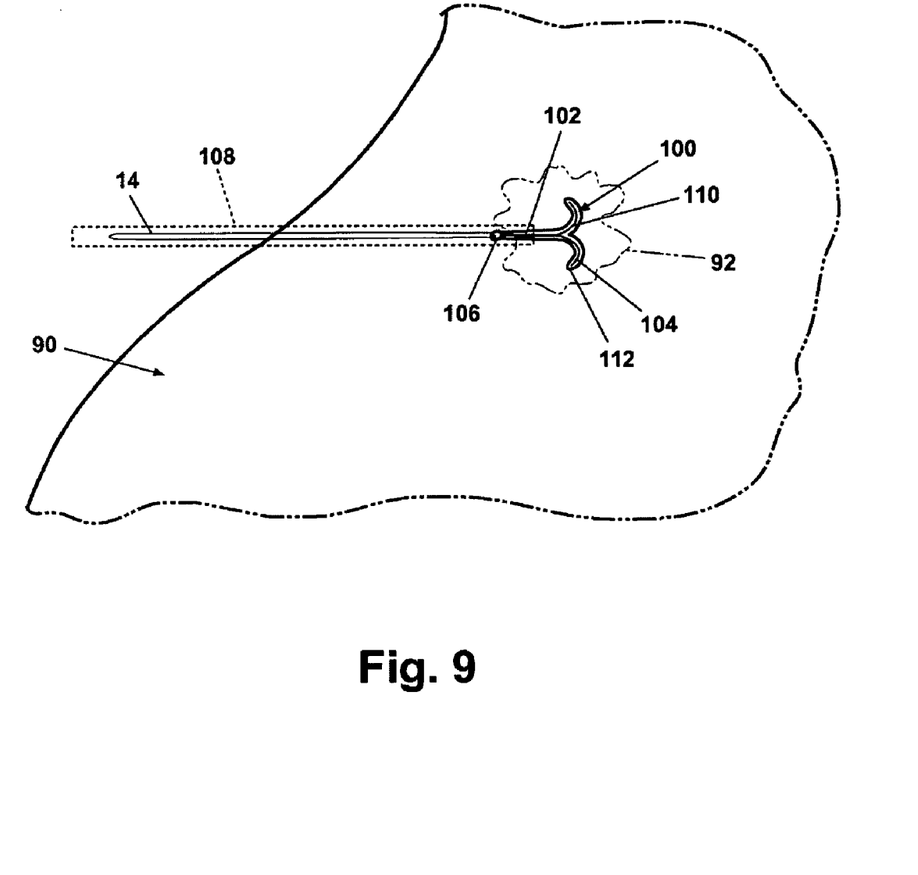
FIG. 9 is an enlarged view of a sixth embodiment of the imaging element comprising a repositionable imaging element comprising a non-bioabsorbable portion and a bioabsorbable portion.

There are circumstances in which it may be necessary to reposition the medical device 10 after initial emplacement. For this purpose, a repositionable imaging element can be used. Illustrated in FIG. 9 is a medical device comprising a repositionable imaging element 100 separably connected to the guide element 14, which is illustrated as a filament loop, through a releasable connection 106, illustrated as a ring-like body. The imaging element 100 is shown as a somewhat Y-shaped body comprising a shaft 102 terminating in a pair of opposed hooks 104. The imaging element 100 is illustrated as comprising a bioabsorbable portion 110 and a non-bioabsorbable portion 112 similar to the imaging elements previously described herein.

The non-bioabsorbable portion 112 preferably comprises a high-strength flexible metallic wire of suitable strength and flexibility for the purposes described herein, such as stainless steel, titanium, or a nickel-titanium alloy, such as Nitinol, which has shape memory characteristics. The bioabsorbable portion 110 comprises a material such as collagen or gelatin, as previously described herein. The non-bioabsorbable portion 112 has sufficient rigidity to securely anchored the imaging element 100 in the lesion 92. However, if it is necessary to reposition the medical device 10, the hooks 104 can deflect in order to disengage the imaging element 100 from the lesion 92 and enable the imaging element 100 to be repositioned.

The imaging element 100 is designed to be easily viewable under at least one of the common imaging techniques. In this manner, the imaging element is different from prior art hook devices that were used solely as anchors for a localizing wire. Advantageously, the imaging element 100 is several times larger than the previously described imaging elements. The larger size of the imaging element 100 and the multiple hooks thus provide the imagable element 100 with a much greater holding force than the previously described imaging elements.

As shown in FIG. 9, a well-known repositioning cannula 108 is typically utilized for the repositioning procedure. The cannula 108 is introduced into the tissue mass 90 with the guide element 14 extending therethrough until the cannula 108 encounters the imaging element 100. As the cannula 108 is further translated relative to the hooks 104, the hooks 104 engage the end of the cannula 108 and are elastically deflected. The imaging element 100 can be recovered into the lumen of the cannula 108 by continued insertion of the cannula 108 into the tissue mass 90, by pulling the guide element 14 to urge the imaging element 100 into the lumen, or a combination of both. With the imaging element 100 removed from the lesion 92 into the cannula 108, the cannula 108 can be repositioned for reinsertion of the imaging element 100 into the lesion. Should further medical evaluation indicate no need for surgical intervention, the guide element 14 can be removed from the imaging element 100 as previously described, which enables the complete removal of the medical device without separating the guide element from the imaging marker.

The repositionable imaging element 100 is typically larger than the imaging elements previously described herein. Thus, it may be desirable to recover the imaging element 100 from the lesion 92, rather than allowing the imaging element to remain in place as with the previously described embodiments. Thus, while the guide element 14 is attached to the imaging element 100 through the releasable connection 106 for separation of the guide element 14 from the imaging element 100 as previously described, the use of a repositionable imaging element 100 enables the medical device 10 to be recovered from the patient in its entirety. Furthermore, there may be unforeseen circumstances in which removal of the imaging element is very difficult or dangerous to the patient, or cannot be accomplished because of the failure of the releasable connection to properly separate. In anticipation of these circumstances, the repositionable imaging element 100 can be incorporated into the medical device 10 for both separation from the guide element 14, or complete removal.

The medical device 10 disclosed herein enables a physician to place, in effect, an imageable marker and a localizing wire at the same time during the core biopsy procedure. By placing the apparatus 10 at the site of the core biopsy, the site is marked with a secure device that can be easily visualized during subsequent imaging techniques. The separable guide element 14 is already in place shall a core biopsy pathology indicate surgical intervention. This eliminates the need for a separate wire localization procedure. If the core biopsy pathology indicates no need for surgical intervention, the physician can simply separate the guide element 14 from the imaging element 12, and remove the guide element 14 from the patient. The imaging element 12 remains in place to mark the site of the biopsy as with current imaging devices.

While the invention has been specifically described in connection with certain specific embodiments thereof, it is to be understood that this is by way of illustration and not of limitation. Reasonable variation and modification are possible within the scope of the forgoing disclosure and drawings without departing from the spirit of the invention which is defined in the appended claims.

The invention claimed is:

1. A medical device, comprising:
an imaging element for subcutaneous placement in a tissue mass via a delivery apparatus adapted to penetrate the tissue mass, the imaging element adapted to identify an area of interest in the tissue mass; and
a guide element having, when the guide element is intact: (i) a first end coupled to the imaging element, (ii) a second end distal from the imaging element, and (iii) a separable portion that includes at least the second end;
wherein the first end of the guide element is adapted to be coupled to the imaging element, and the second end is adapted to extend exteriorly to the tissue mass, after the delivery apparatus has been removed from the tissue mass;
wherein the separable portion is removable from the tissue mass after the delivery apparatus has been removed from the tissue mass, and wherein the guide element is adapted to not exteriorly to the tissue mass after the separable portion has been removed from the tissue mass.

2. The medical device according to claim 1, wherein the separable portion comprises the entire guide element.

3. The medical device according to claim 1, wherein the imaging element can be imaged by at least one of the following imaging techniques:
x-ray,
ultrasound,
magnetic resonance imaging (MRI),
computer assisted tomography (CAT),
mammography,
fluoroscopy,
Doppler,
other roentgenological imaging methods,
visualization, and
detection of emission.

4. The medical device according to claim 1, wherein the imaging element comprises a portion that is bioabsorbable.

5. The medical device according to claim 4, wherein the guide element is bioabsorbable.

6. The medical device according to claim 1, wherein the imaging element comprises a first portion that is non-bioabsorhable and a second portion that is bioabsorbable, 7. The medical device according to claim 6, wherein the first portion comprises titanium.

8. The medical device according to claim 6, wherein the second portion comprises collagen.

9. The medical device according to claim 1, wherein the imaging element further comprises at least one extension.

10. The medical device according to claim 9, and further comprising a bioabsorbable element mounted to the extension.

11. The medical device according to claim 10, wherein the bioabsorbable element encapsulates at least a portion of the extension.

12. The medical device according to claim 1, wherein the imaging element defines a guide element opening through which the guide element passes.

13. The medical device according to claim 12, wherein the imaging element comprises a loop that defines the guide element opening.

14. The medical device according to claim 13, wherein the guide element is a filament.

15. The medical device according to claim 14, wherein the filament is made from suture material.

16. The medical device according to claim 14, wherein the filament is a metal wire.

17. The medical device according to claim 1, and further comprising a holder mounted to a portion of the guide element exterior of the tissue mass to hold the position of the guide element relative to the tissue mass.

18. The medical device according to claim 1, and further comprising a releasable connection connecting the guide element to the imaging element to form the separable portion.

19. The medical device according to claim 18, wherein the releasable connection comprises a threaded coupling.

20. The medical device according to claim 18, wherein the releasable connection is a weldment.

21. The medical device according to claim 18, wherein the releasable connection is a severable portion of the guide element.

22. The medical device according to claim 18, wherein the releasable connection is a discontinuity in the guide element.

23. The medical device according to claim 1, and further comprising a gripping element attachable to the guide element for separating the guide element from the imaging element.

24. The medical device according to claim 1, wherein the imaging element is releasable to permit the repositioning of the imaging element in the tissue mass.

25. The medical device of claim 24 wherein the imaging element comprises at least one flexible hook.

26. The medical device according to claim 1, wherein the guide element is a filament.

27. The medical device according to claim 26, wherein the filament comprises a length of wire.

28. The medical device according to claim 26 wherein the filament comprises a length of suture material.

29. The medical device according to claim 1, wherein the guide element comprises a bioabsorbable material.

30. The medical device according to claim 1, wherein the imaging element comprises a portion that is non-bioabsorbable.

31. A method for localizing and marking an area of interest in a tissue mass, comprising the steps of:
provide a medical device comprising an imaging element and a guide element connected to the imaging element; and
inserting the medical device into the tissue mass so that at least part of the guide element extends exteriorly of the tissue mass; and
after the imaging element has been deployed within the tissue mass and a delivery apparatus used to deploy the imaging element has been removed from the tissue mass, removing at least a portion of the guide element so that no portion of the guide element extends exteriorly of the tissue mass.

32. The method according to claim 31, and further comprising the step of unthreading the at least a portion of the guide element to remove the at least a portion of the guide element.

33. The method according to claim 31, and further comprising the step of pulling the guide element to remove the at least a portion of the guide element.

34. The method according to claim 33, wherein the removing step comprises cutting the guide element.

35. The method according to claim 34, wherein the removing step further comprises removing a cut portion of the guide element.

36. The method according to claim 33, wherein the removing step comprises removing the entire guide element from the tissue mass.

37. The method according to claim 33, wherein the removing step comprises separating at least a portion of the guide element from the imaging element.

38. The method according to claim 37, wherein the removing step comprises removing the entire guide element from the tissue mass.

39. The method according to claim 33, wherein the removing step comprises separating the guide element from the imaging element at a spot weld.

40. The method according to claim 31, and further comprising the step of locating the imaging element by an imaging technique.

41. The method according to claim 40, and further comprising the step of removing the at least a portion of the guide element after the locating of the imaging element.

42. The method according to claim 31, and further comprising the step of locating the area of interest in the tissue mass for surgical excision by following the guide element to the imaging element.

43. A delivery apparatus for the percutaneous placement of a medical device at an area of interest in a tissue mass to facilitate subsequent determination of the area of interest, comprising:
an introducer defining a lumen having a proximal end and a distal end defining an expulsion opening;
a piston having a distal end slidably received within the lumen, wherein when the delivery apparatus is in a ready position, the distal end of the piston is spaced inwardly from the expulsion opening to form a recess between the distal end of the piston and the expulsion opening; and
a medical device comprising:
an imaging element positioned in the recess for subcutaneous placement in a tissue mass to identify an area of interest in the tissue mass; and
a guide element having, when the guide element is intact:
(i) a first end coupled to the imaging element, (ii) a second end distal from the imaging element, and (iii) a separable portion that includes at least the second end;
wherein the first end of the guide element is adapted to be coupled to the imaging element, and the second end is adapted to extend exteriorly to the tissue mass, after the delivery apparatus has been removed from the tissue mass; and
wherein when the piston is advanced into the recess, at least the imaging element is expelled through the expulsion opening into the tissue mass, wherein the separable portion is removable from the tissue mass after the delivery apparatus has been removed from the tissue mass, and wherein the guide element is adapted to not extend exteriorly to the tissue mass after the separable portion has been removed from the tissue mass.

44. The delivery apparatus according to claim 43, wherein the introducer comprises a cannula defining the lumen and the piston comprises a stylet.

45. The delivery apparatus according to claim 44, and further comprising a handle to which the cannula is mounted.

46. The delivery apparatus according to claim 45, wherein the handle, cannula, stylet, and medical device are operably coupled such that they form a self- contained marking apparatus that can be handled by a user to effect operation of the delivery apparatus to expel the medical device.

47. The delivery apparatus according to claim 46, wherein the guide element comprises a bioabsorbable material.

48. The delivery apparatus according to claim 46, and further comprising a releasable connection connecting the guide element to the imaging element to form the separable portion.

49. The delivery apparatus according to claim 48, wherein the releasable connection comprises a threaded coupling.

50. The delivery apparatus according to claim 48, wherein the releasable connection is a weldment.

51. The delivery apparatus according to claim 48, wherein the releasable connection is a severable portion of the guide element.

52. The delivery apparatus according to claim 48, wherein the releasable connection is a discontinuity in the guide element.

53. The delivery apparatus according to claim 43, wherein the separable portion comprises the entire guide element.

54. The delivery apparatus according to claim 43, wherein the imaging element can be imaged by at least one of the following imaging techniques:
x-ray,
ultrasound,
magnetic resonance imaging (MRI),
computer assisted tomography (CAT),
mammography,
fluoroscopy,
Doppler,
other roentgenological imaging methods,
visualization, and
detection of emission.

55. The delivery apparatus according to claim 43, wherein the imaging element comprises a portion that is one of bioabsorbable [or] and non-bioabsorbable.

56. The delivery apparatus according to claim 55, wherein the guide element is bioabsorbable.

57. The delivery apparatus according to claim 55, wherein the imaging element comprises a first portion that is non-bioabsorbable and a second portion that is bioabsorbable.

58. The delivery apparatus according to claim 43, wherein the imaging element further comprises at least one extension.

59. The delivery apparatus according to claim 58, and further comprising a bioabsorbable element mounted to the extension.

60. The delivery apparatus according to claim 43, wherein the imaging element defines a guide element opening through which the guide element passes.

61. The delivery apparatus according to claim 60, wherein the imaging element comprises a loop that defines the guide element opening.

62. The delivery apparatus according to claim 61, wherein the guide element is a filament.

63. The delivery apparatus according to claim 43, and further comprising a holder mounted to a portion of the guide element exterior of the tissue mass to hold the position of the guide element relative to the tissue mass.

64. The delivery apparatus according to claim 43, wherein the guide element is a filament.

65. The delivery apparatus according to claim 64, wherein the filament comprises a length of wire.

66. The delivery apparatus according to claim 64, wherein the filament comprises a length of suture material.

67. The delivery apparatus according to claim 43, and further comprising a gripping element attachable to the guide element for separating the guide element from the imaging element.

68. The delivery apparatus according to claim 43, wherein the imaging element is releasable to permit the repositioning of the imaging element in the tissue mass.

69. The delivery apparatus of claim 68 wherein the imaging element comprises at least one flexible hook.

* * * * *